US007179591B2

(12) United States Patent
Foote

(10) Patent No.: US 7,179,591 B2
(45) Date of Patent: Feb. 20, 2007

(54) METHOD AND APPARATUS FOR COMBINATORIAL CHEMISTRY

(75) Inventor: Robert S. Foote, 105 Elliott Cir., Oak Ridge, TN (US) 37830

(73) Assignee: Robert S. Foote, Oak Ridge, TN (US)

( * ) Notice: Subject to any disclaimer, the term of this patent is extended or adjusted under 35 U.S.C. 154(b) by 903 days.

(21) Appl. No.: 09/859,028

(22) Filed: May 16, 2001

(65) Prior Publication Data

US 2001/0029028 A1     Oct. 11, 2001

Related U.S. Application Data

(63) Continuation of application No. 09/305,591, filed on May 5, 1999, now abandoned.

(51) Int. Cl.
*C12Q 1/68* (2006.01)
(52) U.S. Cl. .................... 435/6; 435/7.1; 536/25.3; 530/333
(58) Field of Classification Search .............. 435/7.1
See application file for complete search history.

(56) References Cited

U.S. PATENT DOCUMENTS

| 4,820,504 | A | * | 4/1989 | Battifora ....................... 424/3 |
| 5,143,854 | A | | 9/1992 | Pirrung et al. |
| 5,424,186 | A | * | 6/1995 | Fodor et al. .................. 435/6 |
| 5,639,603 | A | * | 6/1997 | Dower et al. ................. 435/6 |
| 5,661,028 | A | * | 8/1997 | Foote ..................... 435/287.2 |
| 5,763,263 | A | * | 6/1998 | Dehlinger ................. 435/287 |
| 5,798,035 | A | * | 8/1998 | Kirk et al. .................. 205/335 |
| 6,037,186 | A | * | 3/2000 | Stimpson ................... 436/518 |
| 6,083,697 | A | * | 7/2000 | Beecher et al. ............. 435/6 |
| 6,426,184 | B1 | * | 7/2002 | Gao et al. .................... 435/6 |

FOREIGN PATENT DOCUMENTS

| EP | 0196174 A2 | * | 1/1986 |
| EP | 373203 | | 8/1994 |
| WO | 93/09668 | * | 5/1993 |
| WO | WO 93/09668 | | 5/1993 |
| WO | WO 94/08051 | | 4/1994 |
| WO | WO 95/13538 | | 5/1995 |
| WO | WO 95/16209 | | 6/1995 |
| WO | WO 98/20967 | * | 5/1998 |
| WO | 99/19711 | * | 4/1999 |

OTHER PUBLICATIONS

Banerjee et al., Protecting Groups that can be . . . , Journal of Organic Chemistry, v. 62, 6245-6251, 1997.*
Acetic acid, trichloro-, ester with 2-hydroxyacetophenone, CAS reg. No. 90724-05-3, data obtained from CAOLD in STN.*
New Riverside Dictionary p. 248, 1994.*
Derwent Abstract No. 1999-288012 to Milstein WO 9919711, Apr. 1994.*
Beatie et. al., "Advances in genosensor research," *Clinical Chemistry*, 41(5): 700-706, 1995.

Bunin and Ellman, "A general and expedient method for the solid-phase synthesis of 1,4-benzodiazepine derivatives," *J. Am. Chem. Soc.*, 114:10997-10998, 1992.
Bunin et, al., "The combinatorial synthesis and chemical and biological evaluation of a 1,4-benzodiazepine library," *Proc. Natl. Acad Sci. USA*, 91(11):4708-4712, 1994.
Calvert and Pitts, Jr., *Photochemistry*, John Wiley & Sons, New York, pp. 550-555, 1966.
Chen et. al., "Analogous organic synthesis of small-compound libraries: Validation of combinatorial chemistry in small-molecule synthesis," *J. Am. Chem. Soc.*, 116:2661-2662, 1994.
DeWitt. et. al., "Diversomers: An approach to nonpeptide, nonoligomeric chemical diversity," *Proc. Natl. Acad. Sci. USA*, 90:6909-6913, 1993.
Dooley et. al., "Acetalins: Opioid receptor antagonists determined through the use of synthesis peptide combinatorial libraries," *Proc. Natl. Acad. Sci. USA*, 90(22):10811-10815, 1993.
Dooley et. al., "The use of positional scanning synthetic peptide combinatorial libraries for the rapid determination of opioid receptor ligands," *Life Sci.*, 52(18):1509-1517, 1993.
Drmanac et. al., "DNA sequence determination by hybridization: A strategy for efficient large-scale sequencing," *Science*, 260:1649-1652, 1993.
Eichler et. al., "Identification of substrate-analog trypsin inhibitors through the screening of synthetic peptide combinatorial libraries," *Biochemistry*, 32(41):11035-11041, 1993.
Fodor et. al., "Light-directed, spatially addressable parallel chemical synthesis," *Science*, 251:767-773, 1991.
Furka et. al., "General method for rapid synthesis of multicomponent peptide mixtures," *Int. J. Pept. Protein Res.*, 37:487-493, 1991.
Gao et. al., "Oligonucleotide synthesis using solution photogenerated acids," *J. Am. Chem. Soc.*, 120, 12098-12099, 1998.
Geysen et. al., "Use of peptide synthesis to probe viral antigens for epitopes to a resolution of a single amino acid," *Proc. Natl. Acad. Sci. USA*, 81:3998-4002, 1984.
Geysen et. al., "Small peptides induce antibodies with a sequence and structural requirement for binding antigen comparable to antibodies raised against the native protein," *Proc. Natl. Acad. Sci. USA*, 82:178-182, 1985.
Greene and Wuts, In: *Protective Groups in Organic Synthesis*, John Wiley & Sons, Inc., New York, 1991.

(Continued)

*Primary Examiner*—Mark L. Shibuya
*Assistant Examiner*—Jeffrey S. Lundgren
(74) *Attorney, Agent, or Firm*—Luedeka, Neely & Graham, PC

(57) ABSTRACT

A method and apparatus are provided for performing light-directed reactions in spatially addressable channels within a plurality of channels. One aspect of the invention employs photoactivatable reagents in solutions disposed into spatially addressable flow streams to control the parallel synthesis of molecules immobilized within the channels. The reagents may be photoactivated within a subset of channels at the site of immobilized substrate molecules or at a light-addressable site upstream from the substrate molecules. The method and apparatus of the invention find particularly utility in the synthesis of biopolymer arrays, e.g., oligonucleotides, peptides and carbohydrates, and in the combinatorial synthesis of small molecule arrays for drug discovery.

13 Claims, 6 Drawing Sheets

OTHER PUBLICATIONS

Himmelsbach et. al., "the ρ-nitrophenylethyl (NPE) group: A versatile new blocking group for phosphate and aglycone protection in nucleosides and nucleotides," *Tetrahedron*, 40: 59-72, 1984.

Houghten et. al., "Generation and use of synthetic peptide combinatorial libraries for basic research and drug discovery," *Nature*, 354:84-86, 1991.

Houghten et. al., "The use of synthetic peptide combinatorial libraries for the identification of bioactive peptides," *BioTechniques*, 13(3):412-421, 1992.

Kramer et. al., "Simultaneous synthesis of peptide libraries on single resin and continuous cellulose membrane supports: Examples for the identification of protein, metal and DNA binding peptide mixtures," *Pept. Res.*, 6(6):314-319, 1993.

Nestler et. al., "A general method for molecular tagging of encoded combinatorial chemistry libraries," *J. Org. Chem.*, 59:4723-4724, 1994.

Pillai, "Photolytic deprotection and activation of functional groups," *Organic Photochemistry*, Padwa, Ed., Marcel Dekker, Inc., New York, 9: 225-323, 1987.

Pinilla et. al., "Rapid identification of high affinity peptide ligands using positional scanning synthetic peptide combinatorial libraries," *Biotechniques*, 13(6):901-905, 1992.

Pinilla et. al., "Synthetic peptide combinatorial libraries (SPCLs): Identification of the antigenic determinant of β-endorphin recognized by monoclonal anibody 3E7,"*Gene*, 128(1):71-76, 1993.

Southern et. al., Analyzing and comparing nucleic acid sequences by hybridization to arrays of oligonucleotides: Evaluation using experimental models, *Genomics*, 13:1008-1017, 1992.

Turro. In: *Modern Molecular Photochemistry*, The Benjamin/Cummings Publishing Co., Inc., Menlo Park, California, Chapter 10, pp. 362-411, 1978.

New Riverside Dictionary p. 248 1994.

Derwent Abstract No. 1999—288012 To Milstein WO 99/19711 Apr. 1994.

Banerjee et al. Protecting Groups that can be . . . , Journal of Organic Chemistry, v. 62, 6245-6251 1997.

Acetic acid, trichloro-, ester with 2-hydroxyacetophenone, CAS reg. No. 90724-05-3, data obtained from CAOLD in STN 1967.

Beatie et al., "Advances in genosensor research," Clinical Chemistry, 41(5): 700-706, 1995.

Bunin and Ellman, "A general and expedient method for the solid-phase synthesis of 1,4-benzodiazepine derivatives," J. Am. Chem. Soc., 114:10997-10998, 1992.

Bunin et al., "The combinatorial synthesis and chemical and biological evaluation of a 1,4-benzodiazepine library," Proc. Natl. Acad Sci. USA, 91(11):4708-4712, 1994.

Calvert and Pitts, Jr., Photochemistry, John Wiley & Sons, New York, pp. 550-555, 1966.

Chen et al., "Analogous organic synthesis of small-compound libraries: Validation of combinatorial chemistry in small-molecule synthesis," J. Am. Chem. Soc., 116:2661-2662, 1994.

DeWitt et al., "Diversomers: An approach to nonpeptide, nonoligomeric chemical diversity," Proc. Natl. Acad. Sci. USA, 90:6909-6913, 1993.

Dooley et al., "Acetalins: Opioid receptor antagonists determined through the use of synthesis peptide combinatorial libraries," Proc. Natl. Acad. Sci. USA, 90(22):10811-10815, 1993.

Dooley et al., "The use of positional scanning synthetic peptide combinatorial libraries for the rapid determination of opioid receptor ligands," Life Sci., 52(18):1509-1517, 1993.

Drmanac et al., "DNA sequence determination by hybridization: A strategy for efficient large-scale sequencing," Science, 260:1649-1652, 1993.

Eichler et al., Identification of substrate-analog trypsin inhibitors through the screening of synthetic peptide combinatorial libraries,: Biochemistry, 32(41):11035-11041, 1993.

Fodor et al., "Light-directed, spatially addressable parallel chemical synthesis," Science, 251:767-773, 1991.

Furka et al., "General method for rapid synthesis of multicomponent peptide mixtures," Int. J. Pept. Protein Res., 37:487-493, 1991.

Gao et al., "Oligonucleotide synthesis using solution photogenerated acids," J. Am. Chem. Soc., 120, 12098-12099, 1998.

Geysen et al., "Use of peptide synthesis to probe viral antigens for epitopes to a resolution of a single amino acid," Proc. Natl. Acad. Sci. USA, 81:3998-4002, 1984.

Geysen et al., "Small peptides induce antibodies with a sequence and structural requirement for binding antigen comparable to antibodies raised against the native protein," Proc. Natl. Acad. Sci. USA, 82:178-182, 1985.

Green and Wuts, In: Protective Groups in Organic Synthesis, John Wiley & Sons, Inc., New York 1991.

Himmelsbach et al., "The p-nitrophenylethyl (NPE) group: A versatile new blocking group for phosphate and aglycone protection in nucleosides and nucleotides," Tetrahedron,40:59-72, 1984.

Houghten et al., "Generation and use of synthetic peptide combinatorial libraries for basic research and drug discovery," Nature, 354:84-86, 1991.

Houghten et al., "The use of synthetic peptide combinatorial libraries for the identification of bioactive peptides," BioTechniques, 13(3):412-421, 1992.

Kramer et al., Simultaneous synthesis of peptide libraries on single resin and continuous cellulose membrane supports: Examples for the identification of protein, metal and DNA binding peptide mixtures,: Pept. Res., 6(6):314-319, 1993.

Nestler et al., "A general method for molecular tagging of encoded combinatorial chemistry libraries," J. Org. Chem., 59:4723-4724, 1994.

Pillai, "Photolytic deprotection and activation of functional groups," Organic Photochemistry, Padwa, Ed., Marcel Dekker, Inc., New York, 9:225-323, 1987.

Pinilla et al., "Rapid identification of high affinity peptide ligands using positional scanning synthetic peptide combinatorial libraries," Biotechniques, 13(6):901-905, 1992.

Pinilla et al., "Synthetic peptide combinatorial libraries (SPCLs): Identification of the antigenic determinant of β-endorphin recognized by monoclonal anibody 3E7,"Gene, 128 (1):71-76, 1993.

Southern et al., Analyzing and comparing nucleic acid sequences by hybridization to arrays of oligonucleotides: Evaluation using experimental models, Genomics, 13:1008-1017, 1992.

Turro. In:Modern Molecular Photochemistry, The Benjamin/Cummings Publishing Co., Inc., Menlo Park, California, Chapter 10, pp. 362-411, 1978.

* cited by examiner

METHOD AND APPARATUS FOR COMBINATORIAL CHEMISTRY

This application is a continuation of application Ser. No. 09/305,591, filed May 5, 1999, now abandoned.

This invention was made with Government support under Contract No. DE-AC05-96OR22464 awarded by the Department of Energy to Lockheed Martin Energy Research, Inc., and the Government may have certain rights in this invention.

BACKGROUND OF THE INVENTION

1. Field of the Invention

This invention relates generally to methods used for performing combinatorial chemistry and more particularly to a method and apparatus for the parallel synthesis of chemical arrays using spatially addressable photochemical reaction schemes.

2. Description of the Related Art

Currently there is widespread interest in using combinatorial libraries of oligonucleotides, polypeptides, synthetic oligomers and small organic molecules to search for biologically active compounds (Kramer, et al., 1993; Houghten, et al., 1992, 1991; Dooley, et al., 1993a–1993b; Eichler, et al., 1993; Pinilla, et al., 1992, 1993). For example, ligands discovered by screening libraries of these types may be useful in mimicking or blocking natural ligands, or interfering with the naturally occurring interactions of a biological target. They can also provide a starting point for developing related molecules with more desirable properties, e.g., higher binding affinity.

Combinatorial libraries of the types useful in this general application have been formed by various solid-phase or solution-phase synthetic methods. In one approach, beads containing successive precursors to the target compounds that form the library are alternately mixed and separated, with one of a selected number of reagents being added to each group of separated beads at each step (the "split-mix" method: Furka, et al., 1991; Chen et al., 1994; Pham, et al., 1995; Dillard, et al., 1994). Each bead contains only one chemical species, allowing the beads themselves to be used for screening. However, the identity of the species on each bead must be independently determined. Although several methods have been reported for tagging the support beads with molecules more readily analyzable than the library members themselves (e.g., Nestler, et al., 1994; Felder, et al., 1995; Dillard, et al., 1994), the need for separate identification of each species nonetheless limits the usefulness of this approach for the preparation of very large libraries.

Another general approach involves the synthesis of a combinatorial library as a physically segregated array of compounds (Geysen, et al., 1984, 1985; Southern, 1994; Southern, et al., 1992; Bunin, et al., 1992, 1994; DeWitt, et al., 1993). Libraries of compounds have been synthesized on functionalized resins either coated on (Geysen, et al., 1984, 1985; Bunin, et al., 1992, 1994) or contained within (DeWitt, et al., 1993) arrays of pins, with reactions carried out in separate chambers. Using such an approach, the chemical identity of each library element on the array is associated with an addressable position on the array. However, in this method, as with the split-mix method, preparation of large libraries would require an undesirably high number of manipulations and/or a large array of separate reaction vessels or sites.

A method for preparation of potentially high density position-addressable arrays on a planar substrate has been reported (Fodor, et al., 1991; Pirrung, et al., 1992). In this method, applicable primarily to oligomeric compounds, a substrate having photoprotective groups is irradiated, using photolithographic mask techniques, in selected regions only, to deprotect surface active groups in those selected regions. The entire surface is then treated with a solution of a selected subunit, which itself has a photoprotected group, to react this subunit with the surface groups in the photodeprotected regions. This process is repeated to (i) add a selected subunit at each region of the surface, and (ii) build up different-sequence oligomers at known, addressable regions of the surface. This method allows for the synthesis of very large permutation libraries, e.g., $10^4$–$10^6$ compounds, in a position addressable array by parallel subunit addition. For example, in the case of oligonucleotide libraries, each subunit addition step requires only four addition reactions, one for each nucleotide added. Thus, in the production of a library of oligonucleotide compounds where n=8, i.e., a library of 8 mers, 65,536 oligonucleotide compounds can be constructed with a total of 32 reaction steps (8 subunit additions, 4 reactions each).

In cases where the compounds are to be screened for biological activity while still attached to the substrate, this method also allows for rapid screening by binding a reporter-labeled target to the surface and determining the positions of bound target. Surface arrays of this type may be used both for combinatorial library screening (Fodor, et al., 1995; Geysen, et al., 1984, 1985) or for various types of oligonucleotide analysis, such as sequencing by hybridization (Drmanac, et al., 1993; Southern, 1994; Southern, et al., 1992). However, such planar arrays are necessarily limited in the amount (number of molecules) of each library species, since the planar region available to each species is quite small, e.g., on the order of $10^2$–$10^3$ um$^2$. As a consequence, the ability to detect binding species on the array may be limited. Further, it is not feasible to carry out solution-phase screening on a planar array, because of the difficulty of physically separating different array regions carrying different library members.

It would thus be desirable to provide a method and apparatus for preparing a large combinatorial library of compounds which has the advantages of (i) parallel synthesis of subunits in known, addressable library positions, (ii) adaptable to virtually any oligomer or small-molecule chemistry, (iii) a relatively large area for synthesis of each library member, and (iv) screening of individual library compounds in either solution phase or solid phase. The present invention is directed to meeting such objectives, and in doing so, overcoming, or at least reducing the effects of, one or more of the problems set forth above.

SUMMARY OF THE INVENTION

According to one aspect of the present invention, there is provided a method for the synthesis of an array of molecules. The molecules synthesized by this method, e.g., oligonucleotides, peptides, saccharides, small molecules, etc., are immobilized on the inner walls of a plurality of channels and may have distinct chemical compositions or sequences within each of the channels. According to one illustrative method, a plurality of channels are provided which have immobilized on their inner surfaces one or more substrate molecules, the termini of the substrate molecules having protecting groups coupled thereto. A subset of the plurality of channels is exposed to light, for example by directing the light through a photolithographic mask, under conditions which cause a photochemical reaction within the subset of channel effective for removing the protecting groups from the substrate molecules. Once the substrate molecules in a subset of the channels are deprotected in this way, a subunit addition step is performed by providing within the plurality of channels a desired chemical subunit to be coupled to the deprotected substrate molecules. By repeating these steps, a desired array of molecules is formed within the plurality of channels.

The photochemical reaction which occurs in the selected subset of channels exposed to light will preferably involve the conversion of a photoactivatable reagent to a photoactivated reagent, wherein the photoactivated reagent causes the removal, either directly or indirectly, of the protecting groups at the termini of the substrate molecules. For example, acid precursor compounds, e.g., triarylsulfonium hexafluoroantimonates, triarylsulfonium hexafluorophosphates, 2,1,4-diazonaphthoquinone sulfonates, perhalogenated triazines, and the like, are well suited for use as photoactivatable compounds according to this invention. Upon photoactivation within a subset of channels, the photogenerated acid causes the removal of acid labile protecting groups, e.g., dimethoxytrityl groups, from the substrate molecules.

According to another aspect of the invention, an apparatus is provided for use in the construction of an array of molecules. The apparatus generally comprises a plurality of substantially parallel glass or polymeric channels, each of said channels having a first end and a second end. The channels are preferably comprised of substantially parallel capillary tubes, or a microchannel array, wherein the channels have inner diameters in the range of about 1 μm to about 1000 μm. For most applications, the channel diameters will be in the range of about 100 μm to 200 μm, however the apparatus may also be used for making very high-density, closely packed channel arrays with diameters in the range of about 1 μm to 10 μm. At least one fluid chamber, generally having one or more inlet/outlet valves, is continuous with the first and/or second ends of the plurality of channels and is useful for controlling the composition and/or flow of solutions into the plurality of channels. The present apparatus further comprises a means for directing light into a subset of the plurality of channels, e.g., by conventional photolithographic techniques, for effecting photochemical reactions only within the desired subset of channels.

BRIEF DESCRIPTION OF THE DRAWINGS

The invention may be best understood by reference to the following description taken in conjunction with the accompanying drawings, in which like reference numerals identify like elements, and in which.

Figure 1:
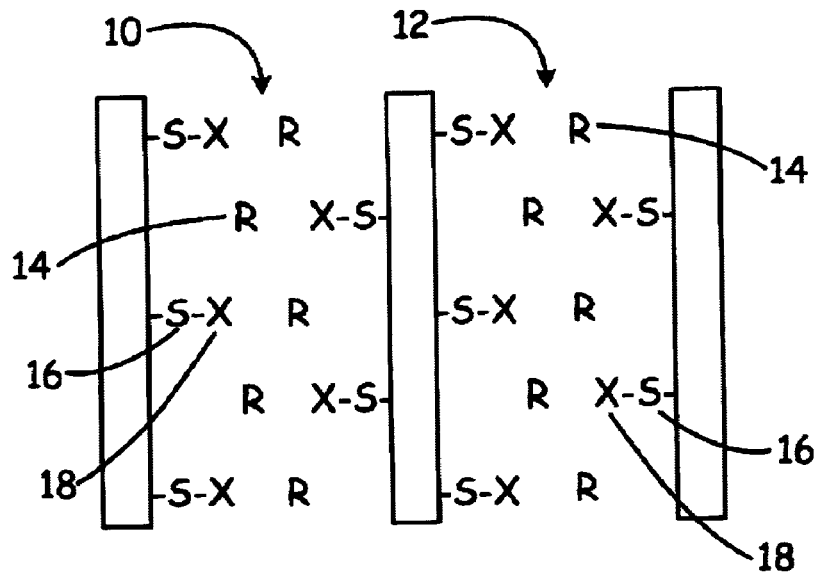
FIGS. 1–3 represent partial cross-sectional views of two adjacent channels in a multichannel array to illustrate one embodiment of the invention in which a photoactivatable reagent is activated in only a subset of channels in the array to cause the selective deprotection of the substrate molecules immobilized within that subset of channels.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
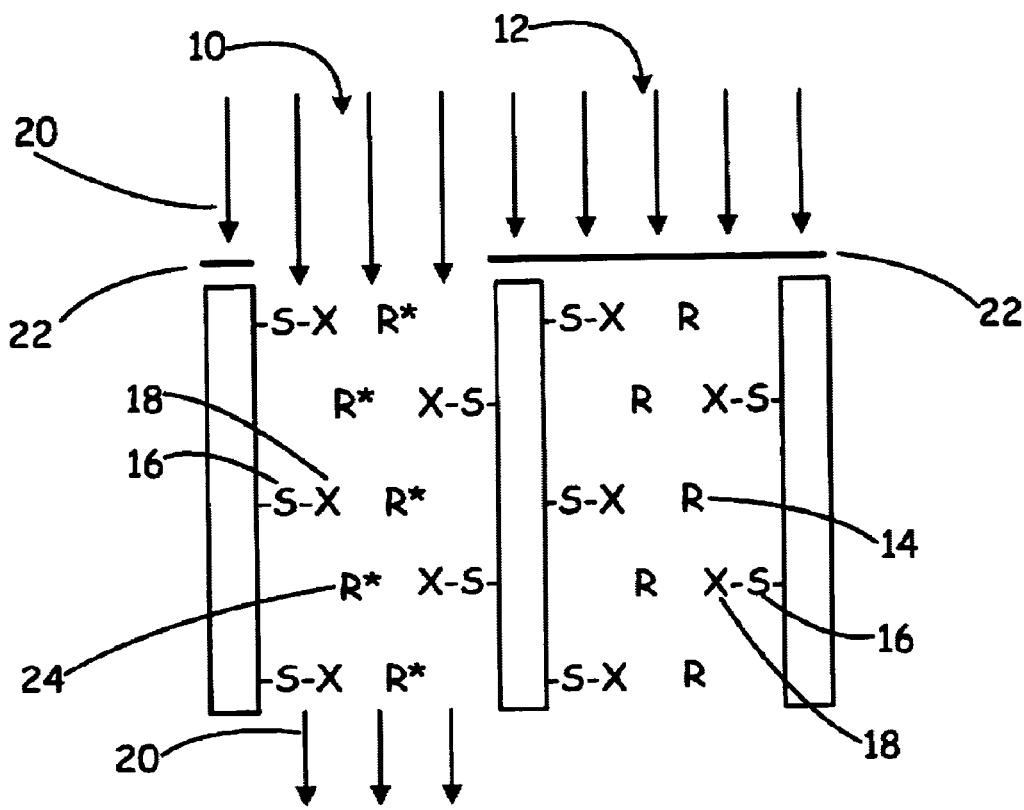
Figure 3:
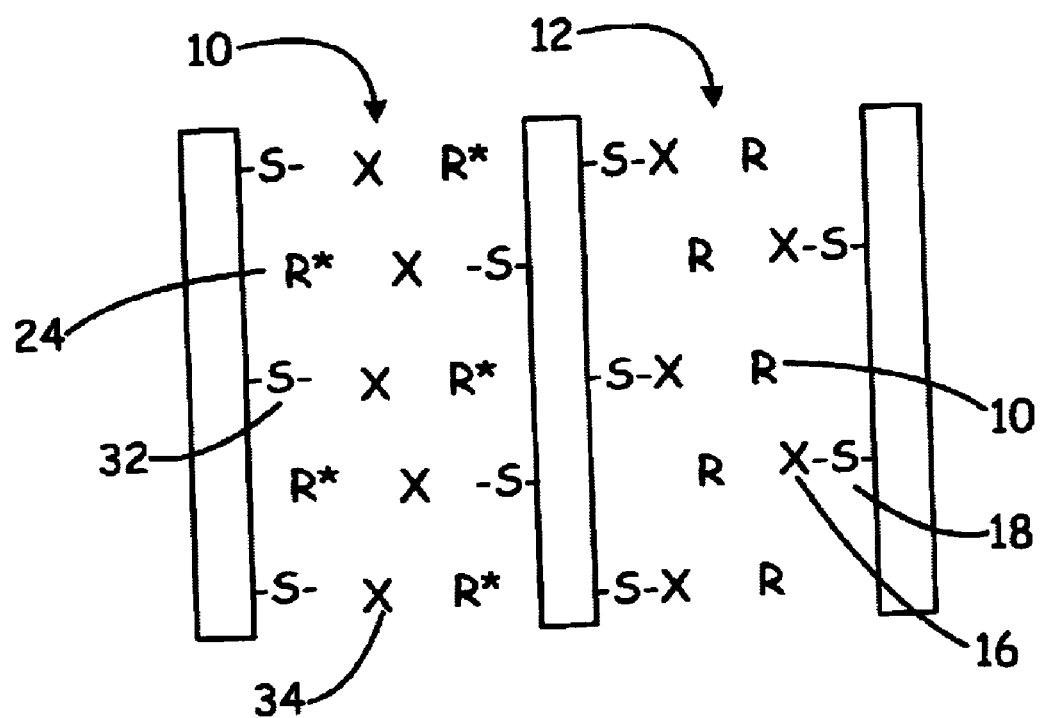

One illustrative method of the present invention is represented in FIGS. 1–3, wherein two adjacent channels 10, 12 in an array of a plurality of channels (not shown) are illustrated at selected intermediate steps during an array synthesis procedure. Turning to FIG. 1, a solution at least partly comprised of a soluble photoactivatable reagent 14 is provided within the channels 10,12. Immobilized on the inner walls of the channels 10,12 are the substrate molecules being synthesized. The substrate molecules (represented as short lines extending inward from the channel walls) will typically have terminal subunits 16 which are protected by protecting groups 18. Protecting groups 18 serve to substantially prevent the terminal subunits 16 from reacting with free subunits that are present within the channels 10,12 during array synthesis.

An immobilized substrate molecule, as the phrase is used herein, can refer to a product of the array synthesis process at essentially any stage during array synthesis. Thus, during the array synthesis process, the terminal subunit 16 of the immobilized substrate molecule will typically represent the chemical subunit most recently added to the substrate molecule in a previous step during array synthesis. For example, during the synthesis of an oligonucleotide array according to this invention, the oligonucleotides bound to the inner surfaces of the plurality of channels represent the immobilized substrate molecules. Depending on the array synthesis step being performed, the immobilized oligonucleotides in the plurality of channels will generally have terminal subunits comprised of the protected nucleotides added in a preceeding subunit addition step. Alternatively, a subset of the plurality of channels may have deprotected nucleotides as their terminal subunits in preparation for the next subunit addition step. Of course, if the reaction being performed is the first subunit addition step in the synthesis procedure, the immobilized substrate may be comprised of a conventional linker compound, a derivative thereof, or another compound suitably bound on the inner surfaces of the channels for use as an immobilized chemical platform for subsequent array synthesis.

Turning to FIG. 2, a light source 20 is directed selectively within a desired channel or subset of channels by use of a mask 22. In this example, the mask 22 allows the light 20 to contact the photoactivatable reagent molecules only in the selected channel 10 but blocks the light from contacting photoactivatable reagent molecules in the other channel 12. The light is provided within the channel 10 at an intensity and for a duration effective for causing the conversion of the photoactivatable reagent 14 to photoactivated reagent 24. As a result of light exposure within the channel 10, photoactivated reagent 24 is produced. The photoactivated reagent 24 then reacts with and causes the removal of the protecting groups 18 from the terminal subunit 16 of the immobilized substrate molecules. This removal, or deprotection step, provides the deprotected terminal subunit 32 of the substrate molecule and releases free protecting group 34 within the channel 10, as represented in FIG. 3.

After performing any desired intermediate steps following deprotection of the terminal groups of the substrate molecules, (e.g., washing steps), a subunit addition step is performed by providing within the channels 10,12 a solution containing the next desired subunits to be reacted with the deprotected terminal subunits 32. As alluded to above, in this subunit addition step, the subunits that are provided within the channels during the subunit addition step will generally be protected, i.e., will have protecting groups coupled thereto such that only a single desired subunit is added to the deprotected terminal subunit 32. Preferably, the subunits that are provided within the channels in the subunit addition step will have protecting groups coupled thereto of the same type that was present on the terminal subunit of the substrate molecule prior to the deprotection step. The subunits are provided in the channels under conditions suitable for reacting with the deprotected terminal subunits 32 within the channel 10, thereby coupling a new protected subunit to the growing substrate molecule within that channel. However, the subunit does not react with the terminal subunits of the substrate molecules immobilized within the other channel 12 since deprotection did not occur in the channel 12. Through repetition of these steps, i.e., mask-mediated deprotection in a subset of channels followed by subunit addition of the deprotected substrates, a desired array of chemical entities can be synthesized within the plurality of channels.

The site-specific application of light to a selected subset of channels in a multichannel array will typically be achieved using a mask, preferably produced by one or more of the numerous photolithographic techniques that are well known in the art. The source of the light directed at the mask and into the desired subset of channels is not critical, and may vary depending on the particular photochemistry involved in the photoactivation step. For many applications, a conventional ultraviolet or visible light source will be suitable provided it can be directed within the selected subset of channels at a sufficient intensity to effect the desired photoactivation reactions. It should be noted that other suitable approaches may be used for directing light into specific channels of the array that do not involve the use of photolithographic masks. For example, light may be selectively directed into the desired subset of channels by a photodoide array having a pattern of light point sources. Alternatively, a light beam, e.g., laser beam, may be scanned over the array such that only the desired subset of channels is irradiated. These and other like techniques will be readily apparent to the skilled individual in this art.

The photoactivatable reagent may be essentially any reagent which, upon light activated conversion to a photoactivated reagent, undergoes or causes a desired reaction within the channel(s) in which it has been activated. Preferably, the photoactivatable reagent is a reagent that upon photoactivation reacts with and causes the removal of protecting groups from the terminal subunits of the immobilized substrate molecules within the channel. Numerous possible photochemical reaction schemes are available and will be readily apparent to the skilled individual in light of this disclosure. These may involve, without limitation, addition reactions, substitution reactions, oxidation reactions, reduction reactions, hydrolysis reactions, and the like. Depending on the requirements and/or preferences for a particular implementation of this embodiment of this invention, suitable photoactivatable reagents may be selected such that, upon photoactivation, the reagent is converted to a desired functionality, e.g., acid, base, thiol reducing agent, alcohol, free radical, or other functionality suitable for reacting with and/or causing the desired removal of protecting groups from the protected terminal subunits of the substrate molecules. For example, the following reaction schemes illustrate certain non-limiting examples of photochemical reactions suitable for converting a photoactivatable reagent to a photoactivated reagent according to the invention:

(1) Photogeneration of Acids:

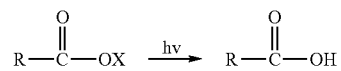

R=H, alkyl, aryl, heteroaryl (e.g., $CH_3$, $CCl_3$, $CF_3$, phenyl)

X=photolabile group (e.g., 2-nitrobenzyl)

(2) Photogeneration of Bases:

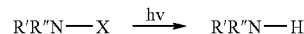

R', R"=H, alkyl, aryl (e.g., $CH_3$, $CCl_3$, $CF_3$, phenyl)

X=photolabile group (e.g., 2-nitrobenzylcarbonyl)

(3) Photogeneration of Thiol Reducing Agents

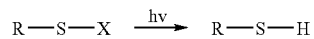

R=alkyl, hydroxyalkyl (e.g., 2-hydroxyethyl)

X=photolabile group (e.g., 2-nitrobenzyl)

(4) Photogeneration of Alcohols (e.g. for Esterification of Immobilized Acids)

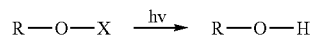

R=alkyl, aryl

X=photolabile group (e.g., 2-nitrobenzyl, 2-nitrobenzylcarbonyl)

(5) Photogeneration of Free Radicals (e.g., for Additions, Displacements, etc.)

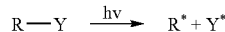

or,

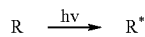

For example:

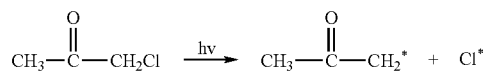

The skilled individual will appreciate that there are many types of photoaddition and photosubstitution reactions suitable for use in the invention, not necessarily limited to these specifically described herein (for example, see Turro, 1978).

In one preferred embodiment of the invention, the photoactivatable reagent is an acid precursor that can be converted to an acid within a channel by a solution photolytic process. In this embodiment, the protecting group on the terminal subunits of the substrate molecules is acid labile. Thus, the acid precursor is converted to a photogenerated acid within the subset of channels exposed to light, and the resulting acid is effective for causing the removal of the acid labile protecting group from the termini of the substrate molecules within the subset of channels. Such photoactivable reagents may include, without limitation, 2-napthol, triarylsulfonium hexafluoroantimonates, triarylsulfonium hexafluorophosphates, 2,1,4-diazonaphthoquinone sulfonates, perhalogenated triazines, N-(2-nitrobenzyloxycarbonyl)piperidine and 2-nitrobenzyl acid esters, derivatives thereof, and other like compounds capable of undergoing light activated conversion to an acidic form. Many such compounds have been reported (see, for example, Gao et al., 1998) and numerous others will be readily apparent to individual skilled in the art of photochemistry. Particularly preferred photoactivatable agents include acid compounds, e.g, trichloroacetic acid or trifluoroacetic acid compounds, having photocleavable carboxyl-protecting groups, such as the various α- and phenyl-substituted 2-nitrobenzyl groups, phenacyl groups, benzoin esters, arylazidoalcohols,2,4-dinitrobenzenesulphenyl groups and N-substituted 2-nitroanilides (see, for example, Pillai, 1987).

The above examples are illustrative only. The selection of photoactivatable reagents will of course vary depending on particular chemical entities being synthesized in the array, on the protecting groups being used in the synthesis strategy, etc. Nonetheless, the chemistries involved in photochemically induced reactions have been well described in the art, and then identification and selection of specific reagents desired for a given implementation can be readily achieved.

The present method may be used in synthesizing a variety of combinatorial library types. These may include, for example, arrays of oligomeric/polymeric compounds, such as different-sequence oligo/polynucleotides, or analogs thereof, different-sequence oligo/polypeptides or analogs thereof, position-substituted oligo/polypeptides, oligo/polysaccharides with different sequences of saccharide subunits, lipopeptides/proteins with different permutations of lipid and/or peptide moieties, glycopeptides/proteins, non-biological oligomers/polymers with different sequence permutations, and the like.

A suitable protecting group may include essentially any chemical group that is removable, either directly or indirectly, by the chemical compound that is photochemically generated within the subset of channels exposed to light. Typically the protecting groups are comprised of chemical entities that are substantially labile to acids, bases, thiols, alcohols, free radicals, and/or other functionalities. Numerous protecting groups will be suitable for use in this invention, e.g., dimethoxytrityl, 9-fluorenylmethoxycarbonyl, t-butyloxycarbonyl, methoxymethyl, t-butoxymethyl, siloxymethyl, tetrahydrofuranyl, 1-ethoxyethyl, monomethoxytrityl, 3-(imidazole-1-ylmethyl)bis(4'4"-dimethoxyphenyl)methyl and 9-(9-phenyl)xanthenyl, and other like compounds apparent to the skilled individual (see, for example Green and Wuts, 1991). The choice of protecting group will of course depend on the objectives of the application and on the particular photoactivatable reagents being used. For example, in situations where an acid labile protecting group is employed, such as a dimethoxytrityl group, the photoactivatable reagent that is used will be one that generates an acid upon exposure to light, wherein the acid is effective for causing the removal of the dimethoxytrityl group.

After the photochemical removal of the protecting groups from the terminal subunits in the subset of channels exposed to light, the channels may be flushed or otherwise treated as necessary to remove any undesired products of the photochemical step. Other manipulations may also be performed if necessary or desired depending on the specifics of a given implementation. Subsequently, one or more non-photochemical reactions, typically referred to herein as subunit addition steps, are performed by providing in the plurality of channels a solution at least partly comprised of one or more of the chemical subunits to be added to the deprotected substrate. The subunits are provided under conditions in which they are chemically coupled to the deprotected termini of the substrate molecules in the channels previously exposed to light, but are not added within the channels which were not exposed to light. The subunit added in the subunit addition step may be essentially any chemical entity capable of reacting with and becoming coupled to the deprotected substrate. In the case where the substrate molecule being synthesized is an oligomer/polymer, e.g., an oligonucleotide or peptide, the subunit added will typically be a monomeric unit of that oligomer/polymer, e.g., a nucleoside or amino acid, respectively.

In one preferred embodiment, the method of the present invention may be used for the synthesis of an oligonucleotide array. The length of the oligonucleotides in the array, i.e., number of nucleotide subunits present, is not limiting. In practice, the inner walls of the plurality of channels within which the array is to be synthesized are suitably derivatized by any of a number of known techniques so as to provide a chemical platform for oligonucleotide synthesis. Methods for derivatizing glass surfaces and other materials for various types of solid-phase syntheses are well known (see, for example, U.S. Pat. Nos. 5,436,327, 5,142,047, 5,137,765 and 4,992,383).

The photoactivatable reagent provided within the plurality of channels in this embodiment may be selected from a wide variety of photoreagents available to the skilled artisan. One preferred class of photoactivatable reagents is comprised of acid precursor compounds which can be converted to acidic species upon exposure to light. For example, 2-nitrobenzyl esters, triarylsulfonium hexafluoroantimonates, triarylsulfonium hexafluorophosphates, 2,1,4-diazonaphthoquinone sulfonates, perhalogenated triazines, and other like compounds, can be photochemically cleaved or activated to produce an acid. Particularly preferred photoactivatable agents include acid compounds, e.g., trichloroacetic and trifluoracetic acid compounds, having photocleavable carboxyl-protecting groups, such as the various α- and phenyl-substituted 2-nitrobenzyl groups, phenacyl groups, benzoin esters, arylazidoalcohols, 2,4-dinitrobenzenesulphenyl groups and N-substituted 2-nitroanilides (see, for example, Pillai, 1987).

Dimethoxytrityl protecting groups are generally preferred in this embodiment of the invention. Dimethoxytrityl groups are widely used for 5'-O protection in conventional oligonucleotide synthesis, and, in addition, the monomethoxytrityl groups have also been used. A number of other acid-labile groups have been used for hydroxyl protection in other types of syntheses, and are similarly suitable for use in this invention. Many of these can be found in Greene and Wuts (1991). Examples of groups that can be cleaved with acetic acids include methoxymethyl(cleaved with trifluoroacetic acid), t-butoxymethyl(trifluoroacetic acid), siloxymethyl(acetic acid), tetrahydrofuranyl(acetic acid) and 1-ethoxyethyl(acetic acid).

The photoactivatable reagent is provided in the plurality of channels which make up the array, and a light source is directed into a desired subset of the channels, preferably using a photolithographic mask. For example, a mercury arc lamp may be used with spectral filtration to prevent transmission of wavelengths shorter than about 320 nm. Preferred wavelengths for this embodiment are in the range of 320–380 nm, preferably 350–370 nm, since wavelengths shorter than ~320 nm can damage oligonucleotide molecules and wavelengths longer than ~380 nm are less efficient for driving the photoreaction. The light is provided at an intensity and for a duration effective for converting the acid precursor to an acidic form. The photogenerated acid is thereby generated in the light-exposed channels and causes removal of the dimethoxytrityl or other protecting groups from the terminal nucleotide of an immobilized oligonucleotide chain. As a result, the terminal nucleotides become reactive, i.e., available for the addition of a new protected nucleoside monomer at their termini. Thus, by providing a protected nucleoside monomer within the plurality of channels, the detritylated termini react with the new protected nucleoside monomer and add it to the growing oligonuclotide chain, while the oligonucleotide chains having terminal nucleotides that were not detritylated (i.e, those that were not exposed to photogenerated acid) do not add the new protected nucleoside monomer. Immobilized oligonucleotide chains in a different subset of channels may then be detritylated using a different photolithographic mask, followed by the addition of a different protected nucleoside monomer. These basic steps may be repeated until a desired array of different-sequence oligonucleotides are synthsized in the plurality of channels.

Alternative chemistries for the phosphite-triester and phosphate-triester synthesis of oligonucleotides are well-known and can also be used in the array synthesis processes described herein. Moreover, the synthesis of arrays of RNA oligomers may be carried out similarly, for example, using analogous ribonucleotide monomers with 2'-O protecting groups.

In other embodiments of the invention, photochemically activated reagents may be used to block functional groups of immobilized substrates in specific channels so that they remain unaltered during subsequent reactions of nonprotected substrates in other channels. Photochemical reactions may also be used to indirectly control blocking of other types of reactions. For example, the protection of primary amines by citraconic anhydride (Dixon and Perham, 1968) may be controlled by altering the pH of the reacting solution. The reaction of the anhydride with an amine to produce an unreactive amide proceeds at pH 8 but is reversible at pH 4. Therefore, photolysis of a photolabile ester to produce an acid to lower the pH of the anhydride solution will prevent the blocking reaction, whereas photolysis of a photolabile carbamate to produce a hindered secondary amine could be used to promote the reaction by increasing the pH of the solution. These and other examples will be readily apparent to the skilled individual in light of this disclosure.

It will be apparent that the specific example described herein is non-limiting and many variations to the method of this invention will be apparent to the skilled individual. For example, as described above, the combinatorial synthesis strategy may be designed such that the subunit addition step provides a chemical species that reacts only with the immobilized substrates which underwent the photochemically induced removal of protecting group. Alternatively, the synthesis strategy may be designed such that the added subunit reacts only in those channels wherein the terminal subunits did not undergo deprotection.

The present invention further provides an apparatus useful for producing combinatorial chemical arrays, e.g., for the production of polymer arrays such as oligonucleotide arrays and oligopeptide arrays. An exemplary apparatus is shown schematically in FIG. 4 and several of the core components of the apparatus are further represented in FIG. 5. A synthesis block 41 containing a plurality of parallel channels 42 is enclosed in a synthesis block housing 43. For simplicity of illustration, the synthesis block is shown here with a low density (5×6) array of widely-spaced, large-diameter channels.

The channels which make up the desired array may be formed by any of a variety of approaches and may take numerous forms and/or geometries. In one illustrative embodiment, the channels are comprised of a pluarility of capillary tubes, e.g., those known in the art for performing capillary electrophoresis, arranged in a highly dense array. Alternatively, the plurality of channels may be comprised of a microchannel array. Although the number, density and specific arrangement of channels in the array is not limiting, the arrays will typically contain greater 100 channels, more typically greater than 1000 channels, and sometimes greater than 10,000 or more channels. The inner diameters of the channels will be less than about 1 mm in most instances, however larger channel diameters will also be useful for some applications. Typically, the channels will be cylindrical, i.e., will have a substantially circular cross-section, and will have inner diameters in the range of about 1 to 500 µm, preferably in the range of about 1 to 100 µm. In addition, high denisty, closely packed arrays having channel diameters in the range of about 1 to 10 µm are also possible in accordance with this invention.

The synthesis block 41 may be made from any of a variety of materials, e.g., glass, polymer, or other suitable materials, depending on the specific application for which the completed array is to be used. For example, a synthesis block made of a polymer material may be preferred where the block is to be cut into thin transverse sections. The inner walls of the synthesis channels 42 are generally chemically modified or otherwise derivatized prior to array synthesis by covalent attachment of suitable linker moieties which serve as the chemical platform for solid-phase synthesis within the channels. For example, the inner walls of the channels 42 may be treated to form chemically reactive surface groups, such as carboxyl, hydroxyl, or amine groups on the inner wall portion and the reactive groups then chemically reacted with a protected linker moiety to which the first subunit may be added at the beginning of array synthesis. Methods for derivatizing glass surfaces for various types of solid-phase syntheses are well known (see, for example, U.S. Pat. Nos. 5,436,327, 5,142,047, 5,137,765 and 4,992,383). In one illustrative example, a linker arm will contain a hydroxyl group which is protected as the dimethoxytrityl ether. Deprotection, i.e., removal of the dimethoxytrityl protecting group, in a specific subset of channels, therefore allows coupling to a first chemical subunit, e.g., the first nucleoside monomer during oligonucleotide array synthesis.

The synthesis block housing 43 is typically made of metal, such as stainless steel, but may be made of any substantially rigid material, including Teflon or other chemically inert plastics. A gasket 44, preferably made of Teflon, silicon rubber or other chemically inert material, separates one end of the synthesis block 41 and synthesis block housing 43 from a transparent plate 45 to create a fluid chamber 46. The fluid chamber 46 is continuous with the ends of the plurality of channels, and is thereby capable of providing a desired solution within the channels. The gasket 44 further provides a seal to prevent fluid leakage between the sides of the housing and synthesis block. The plate 45 is held in place by an end cap 47 which is separated from the plate by a second gasket 48. The end cap may be made of the same material as the synthesis block housing, or another suitable material.

A photolithographic mask 49 is positioned above the transparent plate such that the ends of specific channels may be exposed to light which passes through transparent regions 50 in the mask 49 and therefore through the transparent plate or fluid chamber. Radiation from a light source 51, such as a memory arc lamp or laser, may be spectrally filtered, focused and collimated as necessary to produce essentially monochromatic, collimated light of the desired wavelength. For high-density arrays of channels, the thicknesses of the transparent plate 45 and fluid chamber 46 are preferably minimized to reduce spreading of the light due to refraction. It may be suitable to use microfabricated arrays of lenses in place of the transparent plate to focus the light on the channels, thereby avoiding light speading to nonselected channels. Furthermore, one could expel the liquid from the top chamber 46 and bring the top of the synthesis block into direct contact with the transparent plate 45 during the photoexposure. However, this would not allow continuous flow of reagent into the synthesis block during exposure. Holes in the transparent plate 45, gasket 48 and end cap 47 are aligned to create a first passageway 52 through which fluids may be added to the fluid chamber 46 and a second passageway 53 through which fluids may flow out of the chamber. The flow of fluids into and out of the chamber is controlled by valves 54 and 55, respectively, which may be connected to the passageways by means of tubing 65. A valve 55 may be further connected by means of tubing to a waste receptacle. At the opposite end of the synthesis assembly a second fluid chamber 56 is created by the end plate 57, which is separated from the end of the synthesis block and synthesis block housing by a gasket 58 and held in place by a second end cap 59 and gasket 60. The end plate may be made of glass, metal or any other substantially rigid and chemically inert material. Holes in the end plate 57, the second end cap 59, and the gasket 60, are aligned to create a first passageway 61 for the addition of fluids to the chamber 56 and second passageway 62 through which fluids may flow out of the chamber. The flow of fluids through passageways 61 and 62 is controlled by valves 63 and 64, respectively, which are connected to passageways by means of tubing to a pump or other device for adding solvents to the fluid chamber, 56, and valve 64 is connected by means of tubing to a waste receptacle. The synthesis block assembly may be held together by screws or other fasteners (not shown) which connect the end cap 47 to the second end cap 59.

Figure 4:
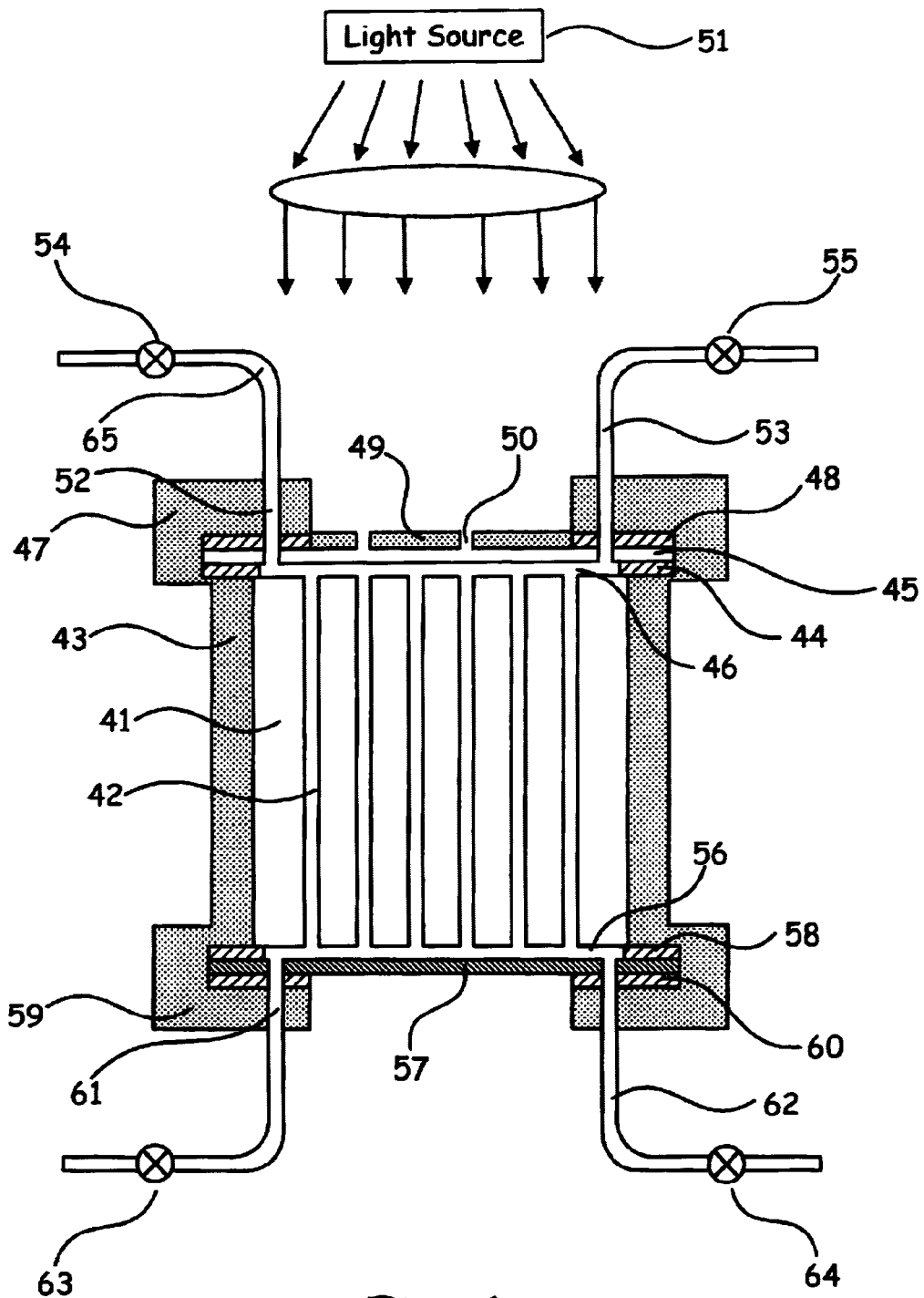
FIG. 4 is a cross-sectional view of an illustrative apparatus used in accordance with the present invention for the synthesis of three-dimensional chemical arrays.
Figure 5:
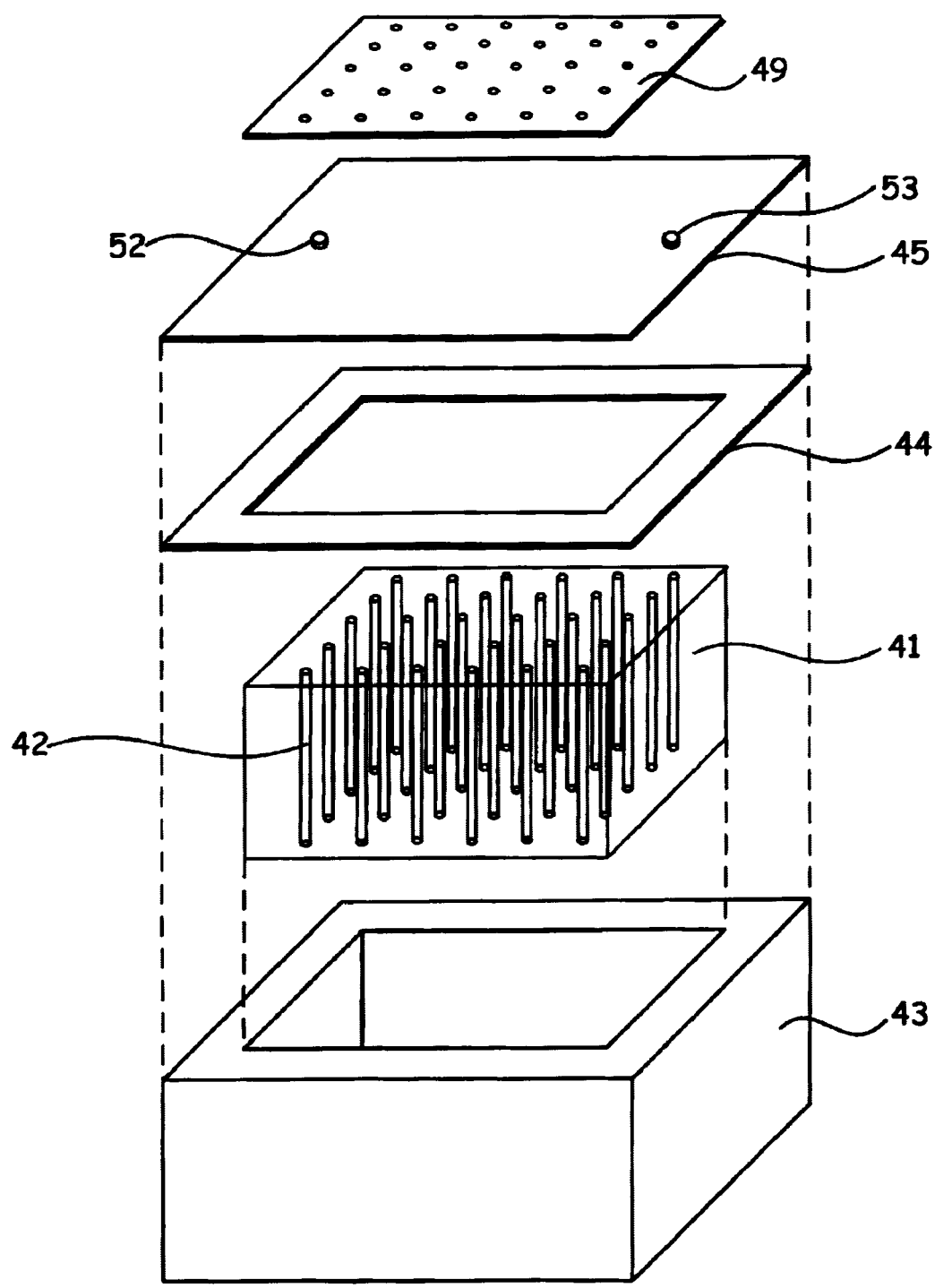
FIG. 5 is a representation of selected components, e.g., synthesis block, synthesis block housing, plurality of channels, etc., of the illustrative apparatus depicted in FIG. 4.

With further reference to FIG. 4, an illustrative combinatorial array synthesis may be carried out in the disclosed apparatus as follows. A solution of photoactivatible reagent is added to the fluid chamber 46 by opening valves 53 and 54 and by use of a pump, syringe or other means of applying hydraulic pressure to the solution (not shown). After the chamber 46 is filled with reagent solution, valve 54 is closed and valve 63 is opened to cause the reagent to flow through the channels of the synthesis block. Light is then directed into the ends of a selected subset of channels in the synthesis block via mask 49 to cause the photoactivation of a photoactivatable reagent within the subset of channels. The solution flow may be discontinued prior to photoactivation in cases where the light is able to pass through to entire length of the channel or a major portion thereof, thereby causing photoactivation of reagent throughout the major portion of the channel. Alternatively, in cases where the light is substantially absorbed in a portion of the channel proximal to the light source, the flow of reagent solution may be continued during all or part of the photoactivation step in order to distribute the photoactivated reagent throughout the length of the channel.

In order to prevent the buildup of photoactivated reagent in fluid chamber 46 which could enter non-selected channels, valve 55 may be partially or intermittently opened in order to add fresh reagent solution to the chamber and to flush photoactivated reagent out of the chamber. Other means will also be suitable to prevent the undesired entry of photoactivated reagent in non-selected channels. For example, following the addition of reagent solution to the synthesis channels 42 and prior to the photoactivation step, the reagent solution can be flushed out of the chamber 46 with solvent which contains no photoactivatable reagent by opening one valve 55 and closing the other valve 63. The valve 63 may be used for flushing reagents from the bottom of fluid chamber 56 and/or for backflushing the synthesis block with solvents. The flushing step will also remove reagent solution from a small portion of the channel proximal to the fluid chamber.

The selected subset of channels are then exposed to light through the mask 49. Because no reagent is present in the fluid chamber, no photoactivated reagent can be formed in the chamber and enter non-selected channels. The steps of reagent addition, solvent flushing and photoactivation can be repeated, if necessary, until the entire length of the selected channels are exposed to photoactivated reagent. Following reaction of photoactivated reagent in the subset of selected channels, a subunit addition step is performed in which a chemical subunit or other moiety is provided in the plurality of channels. The subunit reacts only with substrate molecules within the subset of channels where the photoactivated reagent was generated. A different subset of channels are then selected for reaction with a photoactivated reagent using a different photolithographic mask, and these steps are repeated until the desired array of chemical entities has been synthesized in the plurality of channels. Of course, intermediate nonphotochemical reaction steps may also be included in the total synthesis, as necessary and/or desired.

It will be apparent that there are many variations in the design and operation of the apparatus described above. The fundamental requirements are: (1) a means of controlling the flow of reagents and solvents through the array of channels within the synthesis block, such as a microchannel plate or capillary array, and (2) a means of directing light into specific channels or groups of channels of the synthesis block. Other means of performing these steps may include, for example, the application of electrical voltages to the solutions in fluid chambers 46 and 56 to cause electrokinetic flow through the synthesis block channels, and the use of a focused laser beam to sequentially photoactivate reagents in selected channels by either rastering the synthesis block assembly or scanning the laser beam.

In one illustrative embodiment of the invention, following synthesis of the desired array of chemical entities, the three-dimensional multichannel structure may be sliced into multiple two-dimensional arrays. The total surface area occupied by each chemical entity in a 'two-dimensional' array of this type is given by: Area=$\pi$dh, where d is the diameter of the channel and h is the height (thickness) of the slice. Thus, the area for each member of the array in a slice 10 µm thick with 10 µm diameter channels is 314 µm$^2$, whereas the area for each member of a conventional planar array containing 10 µm diameter spots is only 78.5 µm$^2$, or one-fourth of the area in the 10 µm thick slices. For ligand-binding applications, such as the use of oligonucleotide arrays for hybridization analysis of nucleic acids, the increased probe densities per 10 µm array member results in improved detection of bound target molecules. A synthesis block could potentially yield 1000 10 µm thick arrays per cm of its original length. The sliced sections will preferably have thicknesses in the range of about 1 µm to about 100 µm, more preferably in the range of about 1 µm to about 10 µm, however, thicker array slices, e.g., greater than 100 µm, could also be used for flow through applications such as those described by Beattie et al. Synthesis blocks made of silicon or glass may be sectioned by methods used in the industry for the preparation of silicon wafers or multichannel plates, with precautions to avoid the generation of high temperatures in the processed material. Synthesis blocks made of organic polymers, glass capillaries, composite materials, and the like, may be sliced into thin sections using microtomes or similar devices for slicing such materials. The thin sections may be mounted on slides for durability and ease of handling.

In situations where relatively short channels are used, or where the photoactivated reagents are transparent to the activating wavelengths of light, it may be desired to activate the photoactivatable reagent through essentially the entire length of the channel, e.g., by illuminating a static solution from one end of the channel. In this case, the activating light is able to pass through the entire length of the channel either due to low intrinsic absorbance and/or concentration of the activatable reagent and its photoproducts, or because the photoreaction products are nonabsorbant and allow the light to penetrate further into the solution as the reaction proceeds. For longer channels, or in cases of high reagent or photoproduct absorbance, the reagent may be photoactivated in a portion of the channel proximal to the light source and the activated reagent moved through the length of the channel by fluid transport to the distal end. The reagent flow and photoactivation may be continuous or intermittent until the reaction with the substrate is completed throughout the channel.

In a further embodiment of the invention, the method and/or apparatus described herein may be used to create arrays of biomolecules by activating linker groups in specific channels followed by flowing solutions of desired molecules through the channel block. For example, linker groups bearing a primary amine protected as the monomethyoxytrityl derivative may be deprotected by photogeneration of an acid in a specific channel or channels. Reaction of the deprotected amines with a cross-linking agent, such as glutaraldehyde, would allow attachment of a biomolecule containing a primary amine, e.g., a protein or amino-modified nucleic acid. The biomolecule would attach only to those channels which were initially deprotected. Such steps could be repeated to attach different biomolecules within different channels until a desired array was completed.

Although the embodiments described herein will most typically be used in the fabrication of high-density arrays using individual channels having sub-millimeter diameters, arrays channels having considerably larger diameters could be used for the synthesis of greater quantities of individual products. It may be beneficial to fill such channels with a solid support, such as silica or polymeric microbeads, to increase the synthesis area and product yield. If desired, the photoreactions may be performed in an area of the channel which does not contain the solid suppport material to avoid potential light blockage by the solid support.

The illustrative apparatus is also useful for performing photochemical reactions on a variety of immobilized substrates within the channels. Light directed into individual channels, e.g., by photolithographic or other means, may be propagated through the channel cavity or channel wall by internal reflection. In this way, photochemical reactions may take place on molecules immobilized on the interior surface of the channel by an evanescent wave effect. If desired, the channel cavity could be continuously flushed with a nonabsorbing solvent to remove released photolysis by-products. Capillary arrays made, for example, from tubing having an outer surface or layer with an index of refraction lower than that of the inner wall of the tubing could be used for total internal reflection within the inner wall and to prevent light from leaking between adjacent capillaries. Similarly, the use of solvents or solutions with higher refractive indices than the capillary walls could be used to confine the light to the liquid filled channel cavity. Photochemical reactions in immobilized molecules by direct exposure to light as well as indirect photochemical reactions caused by photoactivation of soluble reagents may therefore be used in the total synthesis of desired compounds in three-dimensional arrays of channels.

The following examples are provided to demonstrate certain illustrative embodiments of this invention. It should be appreciated by those skilled in the art that the techniques disclosed in the examples which follow represent those found by the inventors to function in the practice of the invention and thus can be considered to constitute examples of particular modes for its practice. However, those skilled in the art should, in light of the present disclosure, appreciate that many changes can be made in the specific embodiments which are disclosed and still obtain a like or similar result without departing from the spirit and scope of the invention.

EXAMPLES

Example 1

Light-Induced Deprotection of Dimethoxytrityl-Protected Nucleosides

A solution containing 5'-O-dimethoxytrityl thymidine (1 mM) and 2-napthol (10 mM) in methylene chloride was placed in a quartz cuvette having a 2 mm pathlength and exposed to light from a 200 W high-pressure mercury arc lamp for 10 minutes. The light was passed through bandpass and sharpcut filters to give maximum transmission at ~360 nm wavelength with a cutoff at ~320 nm. The irradiated solution was analyzed by high performance liquid chromatography (HPLC) and compared with a non-irradiated solution stored in the dark for the same period of time. The analyses showed essentially complete (97%) detritylation of the exposed nucleoside to give thymidine and no detritylation of the non-exposed sample. 2-napthol is known to be substantially more acidic in the excited state (S1, pK=3.1) than in the ground state (So, pK=9.5) (Calvert and Pitts, 1966). The efficiency of this reaction is somewhat surprising in view of the short lifetime of the S1 excited state (~10 nanoseconds) and the fact that the triplet (T1) state is not acidic (pK ~8). A similar experiment was performed using 4-nitrophenol (So, pK=7.15) instead of 2-napthol. 4-nitrophenol absorbs strongly at longer wavelengths than does 2-napthol and was exposed using filters for 365 nm maximum transmission with a 345 nm cutoff. Although detritylation of 5'-O-dimethoxytrityl thymidine in the exposed solution proceeded more slowly with this phenol, it continued in the dark for several minutes after the exposure, indicating the formation of a long-lived acidic species.

Example 2

Oligonucleotide Array Synthesis

Figure 6:
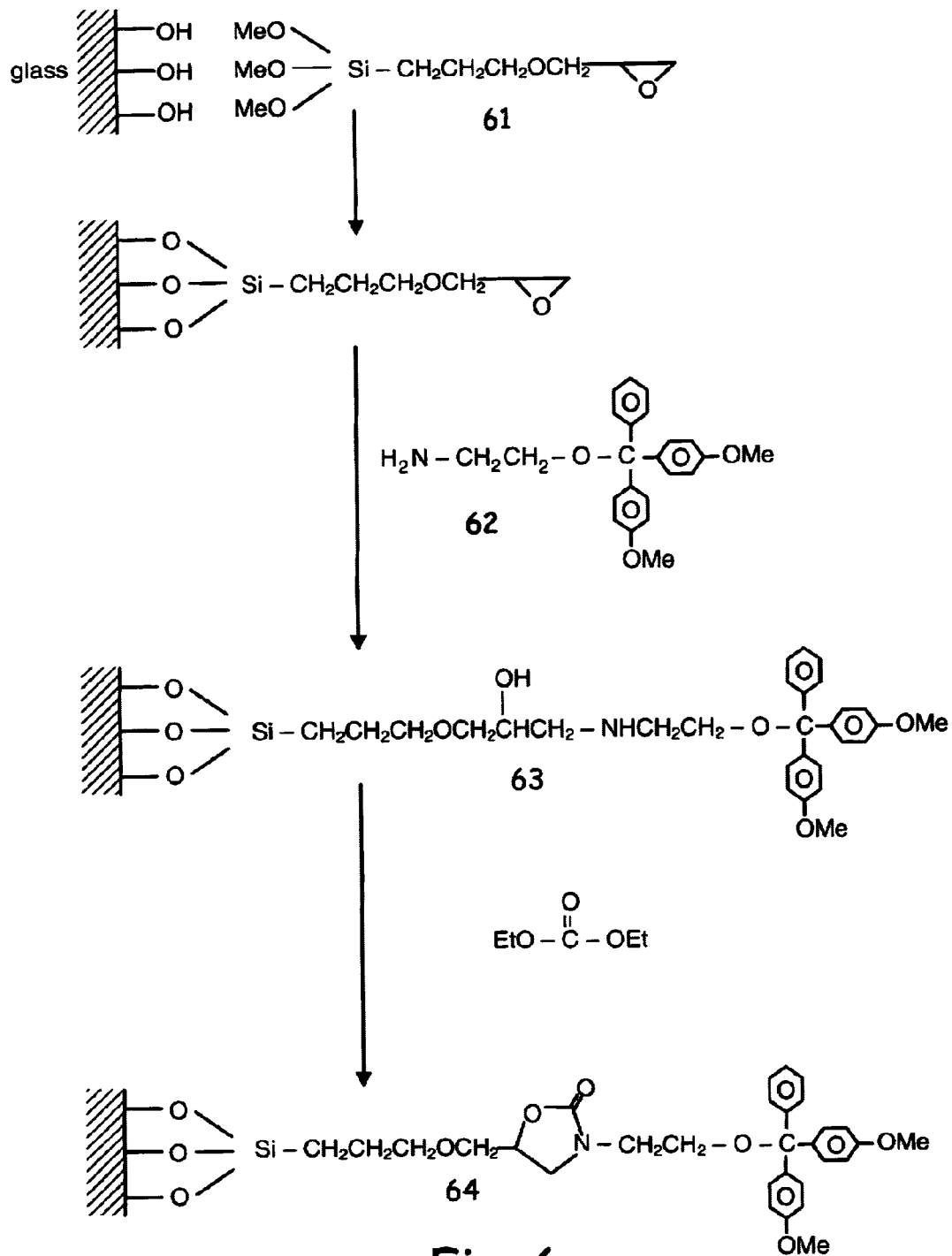
FIG. 6 represents one possible reaction scheme for functionalizing/derivatizing the inner walls of the plurality of channels in preparation for the synthesis of an array of oligonucleotides.

A synthesis block containing parallel glass capillary channels approximately 50 um in diameter and approximately 1 cm in length is used in this example. The inner walls of the channels are first derivatized with linkers bearing a dimethoxytrityl ether which can be deprotected with a photogenerated acid to produce an hydroxyl group for attachment of the first nucleotide. The method for functionalizing the channel walls is shown in FIG. 6. The capillary surfaces are first treated with 3-glycidoxypropyltrimethoxysilane 61 (2% in ethanol). Functionalization of glass surfaces with this reagent is well known. After rinsing the capillaries with ethanol and drying them via purging with inert gas (e.g. nitrogen or argon) the silane coating is allowed to cure at room temperature for several hours or, alternatively, the synthesis block is removed from the apparatus and heated (e.g., at 110° C. for 5–10 minutes) to cure the silane layer. The linker glycidyl groups are then reacted with O-(4,4'-dimethoxytrityl)ethanolamine 62 to give the dimethoxytrityl ether-terminated linker 63. The secondary hydroxyl and amino groups in the linker molecule can be cyclized by reaction with diethyl carbonate or carbonyl chloride to give the fully protected linker 64.

Figure 7:
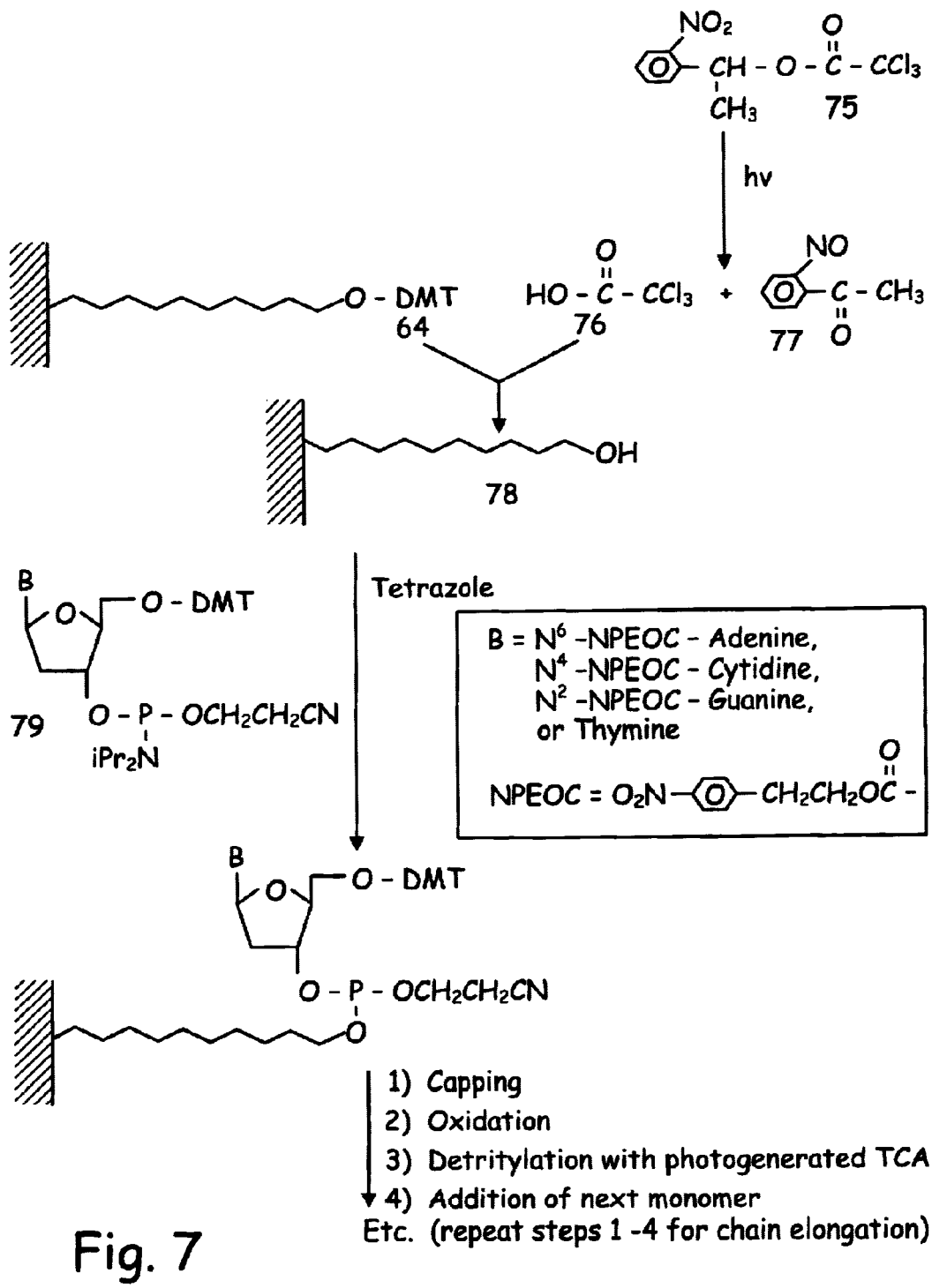
FIG. 7 represents one possible reaction scheme for oligonucleotide synthesis in which the photoactivatable reagant is an acid precursor and the photoactivated reagant is a photogenerated acid.

Dimethoxytrityl (DMT)-protected linkers in selected channels are deblocked by adding a solution of photoactivatable acid to all channels and photogenerating the acid in selected channels by illumination through a mask, as described elsewhere in this application. The detritylation reaction is shown in FIG. 7. A 1–10% (w/v) solution of 1-[2-nitrophenyl]ethyl-1-trichloroacetate 75 in methylenechloride is provided within the channels and illumination of this reagent with ultraviolet light causes its dissociation into trichloroacetic acid 76 and o-nitrosoacetophenone 77. Irradiation in the subset of channels defined/exposed by the mask is provided at an intensity of about ~10–30 mW/cm$^2$ for 5–30 minutes depending on reagent concentration and light intensity to give ~50–100% deprotection of the acid. The light source is a mercury lamp which has a spectral filter to prevent transmission of light shorter than about 320 nm. The acid that is generated within the subset of channels causes detritylation of the DMT ether to produce a terminal hydroxyl group on the linker 78. Following deprotection of the hydroxyl groups in the selected subset of channels, an acetonitrile solution of oligonucleotide synthesis monomer having a 5'-O-DMT protecting group is added to the plurality of channels in the presence of a phosphoramidite activator (e.g., tetrazole) for coupling the protected monomer to the deprotected linkers. Preferred protected monomers for deoxyribonucleic acid synthesis are 5'-O-(4,4'-dimethoxytrityl)-deoxynucleoside-3'-O-(N,N-diisopropylamino-O-cyanoethyl)phosphoramidites 79 in which the exocyclic amine groups are protected as the 4-nitrophenylethoxycarbonyl (NPEOC) derivatives (see, for example, Himmelsbach, 1984). The linker groups in a second set of channels is then deprotected by the above approach and a different monomer is added. These steps are repeated until the linkers of all channels have been reacted with a first monomer.

The steps of monomer addition, capping and phosphite oxidation are carried out using standard reagents and methods for the phosphoramidite synthesis method. The DMT protected 5'-O nucleotide terminus in selected channels is then deprotected with photogenerated acid as in the linker deprotection step. The synthesis steps of monomer addition and deprotection with photogenerated acid are continued using different combinations of masks until all desired sequences in the array are completed. Final deprotection of the exocyclic amines and phosphates is carried by treatment with 0.5 M DBU in dry pyridine for 30–60 minutes at room temperature to remove the NPEOC and cyanoethyl groups without cleavage of the linker.

The particular embodiments disclosed above are illustrative only, as the invention may be modified and practiced in different but equivalent manners apparent to those skilled in the art having the benefit of the teachings herein. More specifically, it will be apparent that certain compounds that are chemically, structurally and/or functionally related to those disclosed herein may be substituted in the methods of this invention while the same or similar results would be achieved. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

REFERENCES

Beatie, K. L., et al., Clinical Chemistry 41: 700–706 (1995).
Bunin, B. A., et al., J. Am. Chem. Soc. 114: 10997–10998 (1992).
Bunin, B. A., et al., Proc. Natl. Acad Sci. USA 91(11): 4708 (1994).
Calvert, J. G and Pitts, Jr., J. N., *Photochemistry*, John Wiley & Sons, New York, 1966, pp. 550.
Chen, C. et al., J. Am. Chem. Soc. 116: 2661–2662 (1994).

DeWitt, S. H. et al., Proc. Natl. Acad. Sci. USA 90: 6909–6913 (1993).
Dillard, L. W. et al., PCT Intl. Appn. Pubn. No. WO 9408051 (4/1994).
Dooley, C. T., et al., Proc. Natl. Acad. Sci. USA 90(22): 10822 (1993a).
Dooley, C. T., et al., Life Sci. 52(18): 1509 (1993b).
Drmanac, et al., Science 260: 1649–1652 (1993).
Eichler, J., et al., Biochemistry 32(41): 11035 (1993).
Felder, E. et al., PCT Intl. Appn. Pubn. No. WO 9516209 (6/1995).
Fodor, S. P. A., et al., Science 251: 767–773 (1991).
Furka, A., et al., Int. J. Pept. Protein Res. 37: 487–493 (1991).
Gao et al., J. Am. Chem. Soc. 120, 12098–99 (1998)
Geysen, H. M., et al., Proc. Natl. Acad. Sci. USA 81: 3998–4002 (1984).
Geysen, H. M., et al., Proc. Natl. Acad. Sci. USA 82: 178–182 (1985).
Greene, T. W. and Wuts, P. G. M., "Protective Groups in Organic Synthesis", John Wiley & Sons, New York, 1991
Himmelsbach, F. et al., Tetrahedron, 40: 59–72, 1984.
Houghten, R. A., et al., Nature 354: 84–86 (1991).
Houghten, R. A., et al., BioTechniques 13: 412–421 (1992).
Kramer, A., et al., Pept. Res. 6(6): 314 (1993).
Nestler, H. P. et al., J. Org. Chem. 59: 4723–4724 (1994).
Pham, E. K. et al., PCT Intl. Appn. Pubn. No. WO 9513538 (5/1995).
Pillai, V. N. R., Organic Photochemistry, 9: 225–323, 1987
Pinilla, C., et al., Biotechniques 13(6): 901 (1992).
Pinilla, C., et al., Gene 128(1): 71 (1993).
Pirrung, et al., U.S. Pat. No. 5,143,854 (1992).
Southern, E., EP Patent No. 373,203 (1994)
Southern, E., et al., Genomics 13: 1008–1017 (1992).
Turro, N. J., "Modern Molecular Photochemistry", Benjamin/Cummings, Menlo Park, 1978, pp. 362–413

What is claimed:

1. A method for the synthesis of combinatorial libraries of oligonucleotide arrays comprising:
   (a) providing a housing containing a unitary synthesis block, said unitary synthesis block including an array of microchannels enclosed within the unitary synthesis block having a first end and a second end of the microchannels, wherein each of the microchannels has an inner microchannel surface, the inner surface of each of the microchannels containing immobilized substrate molecules comprised of oligomeric or polymeric molecules thereon wherein the termini of said substrate molecules have protecting groups coupled thereto;
   (b) providing a light source and a mask for selectively illuminating microchannels in the array;
   (c) flowing a photoactivatable reagent through the array of microchannels from the first end to the second end while selectively illuminating at least a portion of the microchannels from an end thereof, to provide photoactivated reagent in the selectively illuminated microchannels;
   (d) removing protecting groups from the termini of the substrate molecules using the photoactivated reagent thereby forming deprotected substrate molecules in the selectively illuminated microchannels;
   (e) reacting the deprotected substrate molecules with one or more nucleoside monomers under conditions effective for coupling the nucleoside monomers with the deprotected substrate molecules; and
   (f) repeating steps (c) through (e) until a desired oligonucleotide array is formed within the microchannels.

2. The method of claim 1 wherein said photoactivated reagent is an acid precursor.

3. The method of claim 1 wherein the photoactivatable reagent is selected from the group consisting of triarylsulfonium hexafluoroantimonates, triarylsulfonium hexafluorophosphates, 2,1,4-diazonaphthoquinone sulfonates, perhalogenated triazines, and a trihaloacetic acid having a photocleavable carboxyl-protecting group selected from the group consisting of α-and phenyl-substituted 2-nitrobenzyl groups, phenacyl groups, benzoinyl groups, arylazidoalkyl alcohol groups, 2,4-dinotrobenzenesulphenyl groups and N-substituted nitroanilido groups.

4. The method of claim 1 wherein said protecting groups are acid labile protecting groups.

5. The method of claim 1 wherein said protecting groups are selected from the group consisting of dimethoxytrityl, methoxymethyl, t-butoxymethyl, siloxymethyl, tetrahydrofuranyl, 1-ethoxyethyl, monomethoxytrityl, 3-imidazol-1-ylmethyl)bis(4'4"-dimethoxyphenyl)methyl, 9-(9-phenyl) xanthenyl, 9-flurenyl methoxycarbonyl and t-butyloxycarbonyl.

6. The method of claim 1 further comprising slicing the synthesis block containing oligonucleotide arrays into relatively thin sections having a thickness ranging from about 1 micron to about 100 microns to provide a plurality of planar sections of oligonucleotide arrays.

7. The method of claim 1 wherein the microchannels contain a solid support material.

8. A method for the synthesizing oligonucleotide arrays comprising the steps of:
   (a) providing a housing containing a unitary channel array enclosed within a synthesis block including a plurality of channels, each of the channels having a fluid inlet end, a fluid exit end and an inner surface between the inlet end and the exit end;
   (b) attaching substrate molecules to inner surface of the channels so that the substrate molecules have a first end attached to the inner surface of the channels and a second end having protecting groups coupled thereto;
   (c) flowing a photoactivatable reagent through the channel array from the inlet end to the exit end of the channels;
   (d) exposing at least a portion of the channels to light from an end thereof sufficient to activate the photoactivatable reagent sufficient to remove protecting groups from the second end of the substrate molecules to form deprotected substrate molecules in the light exposed channels;
   (e) reacting the deprotected substrate molecules with nucleoside monomers to form oligonucleotide arrays on the inner surface of the channels containing the deprotected substrate molecules; and
   (f) repeating steps (c) through (e) to provide a predetermined array of chemical entities in the channel array.

9. The method of claim 8 wherein said activated photoactivatable reagent comprises an acid precursor.

10. The method of claim 8 wherein the photoactivatable reagent is selected from the group consisting of triarylsulfonium hexafluoroantimonates, triarylsulfonium hexafluorophosphates, 2,1,4-diazonaphthoquinone sulfonates, perhalogenated triazines, and a trihaloacetic acid having a photocleavable carboxyl-protecting group selected from the group consisting of α-and phenyl-substituted 2-nitrobenzyl groups, phenacyl groups, benzoinyl groups, arylazidoalkyl alcohol groups, 2,4-dinotrobenzenesulphenyl groups and N-substituted nitroanilido groups.

11. The method of claim 8 wherein said protecting groups are acid labile protecting groups.

12. The method of claim 8 wherein said protecting groups are selected from the group consisting of dimethoxytrityl, methoxymethyl, t-butoxymethyl, sioxymethyl, tetrahydrofuranyl, 1-ethoxyethyl, monomethoxytrityl, 3-imidazol-1-ylmethyl)bis(4'4"-dimethoxyphenyl)methyl, 9-(9-phenyl) xanthenyl, 9-flurenyl methoxycarbonyl and t-butyloxycarbonyl.

13. The method of claim 8 further comprising slicing the microchannel array into relatively thin sections having a thickness ranging from about 1 micron to about 100 microns to provide a plurality of planar sections of oligonucleotide arrays.

* * * * *

UNITED STATES PATENT AND TRADEMARK OFFICE
CERTIFICATE OF CORRECTION

PATENT NO. : 7,179,591 B2 Page 1 of 3
APPLICATION NO. : 09/859028
DATED : February 20, 2007
INVENTOR(S) : Robert S. Foote It is certified that error appears in the above-identified patent and that said Letters Patent is hereby corrected as shown below:

Col. 2, line 18-19, after "library of" delete "8mers" and insert --8-mers--.

Col. 2, line 34, after "$10^2$-$10^3$" delete "um$^2$" and insert --$\mu m^2$--.

Col. 2, line 63, after "the" delete "temini" and insert --termini--.

Col. 4, line 3, delete "reagant" and insert --reagent--.

Col. 4, line 3, after "photoactivated" delete "reagant" and insert --reagent--.

Col. 4, line 61, delete "preceeding" and insert --preceding--.

Col. 5, line 63, delete "photodoide" and insert --photodiode--.

Col. 6, line 46, delete "(e.g., $CH_3$, $CCL_3$, $CF_3$, phenyl)".

Col. 6, line 47, delete "(e.g., 2-nitrobenzylcarbonyl)" and insert --(e.g., 2-nitrobenzyloxycarbonyl)--.

Col. 6, line 66-67, delete "(e.g., 2- nitrobenzyl, 2-nitrobenzylcarbonyl)" and insert --(e.g., 2- nitrobenzyl, 2-nitrobenzyloxycarbonyl)--.

Col. 7, line 27, after "acid" insert --or base--.

Col. 7, line 27, after "precursor" insert --. The acid precursor--.

Col. 7, line 27, delete "that".

Col. 7, line 28, after "acid" insert --and the base precursor can be converted to a base--.

Col. 7, line 29, after "In" delete "this" and insert --one--.

Col. 7, line 35-36, after "channels." delete "Such photoactivable" and insert --Accordingly, photoactivatable--.

Col. 7, line 36, after "limitation," delete "2-napthol" and insert --2-naphthol--.

Col. 7, line 42, after "acidic" insert --or basic--.

Col. 7, line 45, delete "individual" and insert --individuals--.

Col. 7, line 47, delete "e.g," and insert --e.g.,--.

CERTIFICATE OF CORRECTION (continued)
U.S. Pat. No. 7,179,591 B2

Col. 7, line 48, after "caboxyl-protecting" delete "groups" and insert --functions--.

Col. 7, line 50, after "phenacyl groups" delete "benzoin".

Col. 7, line 50-51, delete "arylazidoalcohols,2,4-dinitrobenzenesulphenyl" and insert --benzoinyl groups, arylazidoalkyl groups, 2,4-dinitrobenzenesulphenyl--.

Col. 7, line 51-52, delete "2-nitroanilides" and insert --2-nitroanilido groups--.

Col. 7, line 59, after "and" delete "then" and insert --the--.

Col. 8, line 16-17, delete "3-(imidazole-1-ylmethyl)bis(4'4"-dimethoxyphenyl)methyl" and insert --3-imidazol-1-ylmethyl)bis(4',4"-dimethoxyphenyl)-methyl--.

Col. 8, line 19, delete "Green" and insert --Greene--.

Col. 9, line 50, after "detritylated" delete "(i.e," and insert --(i.e.,--.

Col. 9, line 60-61, after "are" delete "well-known" and insert --well known--.

Col. 10, line 42, after "of a" delete "pluarility" and insert --plurality--.

Col. 10, line 48, after "greater" insert --than--.

Col. 10, line 57, after "high" delete "denisty" and insert --density--.

Col. 11, line 39, after "a" delete "memory" and insert --mercury--.

Col. 11, line 47, after "light" delete "speading" and insert --spreading--.

Col. 13, line 36, after "1000" delete "10 µm" and insert --10-µm--.

Col. 15, line 8, after "and" delete "2-napthol" and insert --2-naphthol--.

Col. 15, line 19, after "non-exposed" delete "sample.2-napthol" and insert --sample. 2-Naphthol--.

Col. 15, line 26, after "of" delete "2-napthol" and insert --2-naphthol--.

Col. 15, line 28, delete "2-napthol" and insert --2-naphthol--.

Col. 15, line 40, after "approximately" delete "50 um" and insert --50 µm--.

Col. 15-16, line 67-1, delete "methylenechloride" and insert --methylene chloride--.

Col. 16, line 60, delete "Beatie" and insert --Beattie--.

Col. 16, line 63, after "Natl." delete "Acad" and insert --Acad.--.

CERTIFICATE OF CORRECTION (continued)
U.S. Pat. No. 7,179,591 B2

Col. 17, line 15, delete "12098-99" and insert --12698-12699--.

Col. 17, line 39, delete "oligonucleotide arrays" and insert --oligonucleotides--.

Col. 17, line 63, after "more" delete "nucleoside" and insert --nucleotide--.

Col. 17, line 64, after "the" delete "nucleoside" and insert --nucleotide--.

Col. 18, line 11, delete "2,4-dinotrobenzenesulphenyl" and insert --2,4-dinitrobenzenesulphenyl--.

Col. 18, line 17-18, delete "methoxymethyl, t-butoxymethyl, siloxymethyl, tertahydrofuranyl, 1-ethoxyethyl".

Col. 18, line 19, after "methyl" insert --and--.

Col. 18, line 20-21, delete "9-flurenyl methoxycarbonyl and t-butyloxycarbonyl.".

Col. 18, line 29, after "for" delete "the".

Col. 18, line 36, after "inner" delete "surface" and insert --surfaces--.

Col. 18, line 38, after "inner" delete "surface" and insert --surfaces--.

Col. 16, line 49, delete "nucleoside" and insert --nucleotide--.

Col. 18, line 49, delete "oligonucleotide arrays" and insert --oligonucleotides--.

Col. 18, line 64, delete "2,4-dinotrobenzenesulphenyl" and insert --2,4-dinitrobenzenesulphenyl--.

Col. 19, line 3-4, delete "methoxymethyl, t-butoxymethyl, sioxymethyl, tetrahydrofuranyl, 1-ethoxyethyl,".

Col. 19, line 5, after "methyl" insert --and--.

Col. 19, line 6-7, delete "9-flurenyl methoxycarbonyl and t-butyloxycarbonyl".

Signed and Sealed this

Twenty-third Day of February, 2010

David J. Kappos
*Director of the United States Patent and Trademark Office*